United States Patent [19]

Iyer et al.

[11] Patent Number: 5,962,674
[45] Date of Patent: *Oct. 5, 1999

[54] SYNTHESIS OF OLIGONUCLEOTIDES CONTAINING ALKYLPHOSPHONATE INTERNUCLEOSIDE LINKAGES

[75] Inventors: Radhakrishnan P. Iyer, Shrewsbury; Theresa Devlin, Jamaica Plain; Ivan Habus, Shrewsbury; Dong Yu, Shrewsbury; Sudhir Agrawal, Shrewsbury, all of Mass.

[73] Assignee: Hybridon, Inc., Milford, Mass.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/606,915

[22] Filed: Feb. 26, 1996

Related U.S. Application Data

[63] Continuation-in-part of application No. 08/518,921, Aug. 24, 1995, Pat. No. 5,614,622, which is a continuation-in-part of application No. 08/457,198, Jun. 1, 1995, abandoned.

[51] Int. Cl.$^6$ .................................................. C07H 21/00
[52] U.S. Cl. .................. 536/25.34; 536/25.3; 536/25.31; 536/25.33; 536/23.1
[58] Field of Search ............................... 536/25.3, 25.31, 536/25.33, 25.34, 23.1

[56] References Cited

U.S. PATENT DOCUMENTS 5,264,566 11/1993 Froehler et al. .

FOREIGN PATENT DOCUMENTS 8700724 10/1988 Netherlands .

WO 93/08296 4/1993 WIPO .

OTHER PUBLICATIONS

Paterson et al. (1977) *Proc. Natl. Sci. Acad. USA* 74:4370–4374.
Zamecnik (1978) *Proc. Natl. Acad. Sci. USA* 75:280–284.
Stephensen (1978) *Proc. Natl. Acad. Sci. USA* 75:285–288.
Temsamani and Agrawal, Antisense Oligonucleotides as Antiviral Agents, In *Advance in Antiviral Drug Design* (Ed.E. de Clercq), JAI Press, vol.2,pp.1–39 (1995).
Agrawal et al. (1995) *Current Opinion in Biotechnology* 6:12–19.
Miller et al. (1986) *Biochemistry* 25:5092–5095.
Agrawal et al. (1987) *Tetrahedron Letters* 28:3539–3542.
Sonveaux in *Methods in Molecular Biology*, vol. 26: Protocols for Oligonucleotides Conjugates pp. 28–36 (S. Agrawal, Ed., Humana Press, 1994.
Beaucage et al. (1992) *Tetrahedron Letters* 48:2223–2311.
Pon (1993) *Methods in Molecular Biology* 20:465–497.
Debenham et al. (1995) *Journal of the American Chemical Society* 117:3302–3303.
Iyer et al. (1995) *Journal of Organic Chemistry* 60:8132–8133.
Madsen et al. (1995) *Journal of Organic Chemistry* 60:7920–7926.

Primary Examiner—James O. Wilson
Attorney, Agent, or Firm—Hale and Dorr LLP

[57] ABSTRACT

The invention provides new reagents and an improved process for synthesizing oligonucleotides that contain methylphosphonate internucleoside linkages. The reagents and process utilize a nucleoside base protecting group that is stable under oligonucleotide synthesis conditions, but which can be removed under more mild conditions than existing protecting groups.

2 Claims, 1 Drawing Sheet

SYNTHESIS OF OLIGONUCLEOTIDES CONTAINING ALKYLPHOSPHONATE INTERNUCLEOSIDE LINKAGES

This is a continuation-in-part of U.S. Ser. No. 08/518, 921, filed Aug. 24, 1995, which is a continuation-in-part of U.S. Ser. No. 08/457,198, filed Jun. 1, 1995, abandoned

BACKGROUND OF THE INVENTION

1. Field of the Invention

The invention relates to modified oligonucleotides that are useful for studies of gene expression and for the antisense therapeutic approach. In particular, the invention relates to the synthesis of such modified oligonucleotides containing alkylphosphonate internucleoside linkages.

2. Summary of the Related Art

Antisense oligonucleotides are becoming increasingly recognized as powerful tools for inhibiting specific gene expression. The potential for using oligonucleotides as inhibitors of specific gene expression in an antisense therapeutic approach was first suggested in three articles published in 1977 and 1978. Paterson et al., Proc. Natl. Acad. Sci. U.S.A. 74: 4370–4374 (1977) discloses that cell-free translation of mRNA can be inhibited by binding a complementary oligonucleotide to the mRNA. Zamecnik and Stephenson, Proc. Natl. Acad. Sci. U.S.A. 75: 280–284 and 285–288 (1978) disclose that a 13-mer synthetic oligonucleotide that is complementary to a part of the Rous sarcoma virus (RSV) genome can inhibit RSV replication in infected cell cultures and can inhibit RSV-mediated transformation of primary chick fibroblasts into malignant sarcoma cells.

Since these early studies, the ability of antisense oligonucleotides to inhibit virus propagation has become firmly established. Temsamani and Agrawal, *Antisense Oligonucleotides as Antiviral Agents*, In *Advances in Antiviral Drug Design* (Ed. E. de Clercq), JAI Press, Vol. 2, pp. 1–39 (1995), reviews the use of antisense oligonucleotides as antiviral agents. More recently, antisense oligonucleotides have also been developed as anti-parasitic agents and have shown promise as candidates for therapeutic applications for diseases resulting from expression of cellular genes. The development of various antisense oligonucleotides as therapeutic and diagnostic agents has recently been reviewed by Agrawal and Iyer, Current Opinion in Biotechnology 6: 12–19 (1995).

As interest in the antisense therapeutic approach has grown, various efforts have been made to improve the pharmacologic properties of oligonucleotides by modifying the sugar-phosphate backbone. Agrawal and Iyer, Curr. Op. Biotech 6: 12–19 (1995) reviews the use of methylphosphonate linkages in oligonucleotides. Although oligonucleoside methylphosphonates have shown serious limitations as antisense agents, chimeric oligonucleotides containing methylphosphonate linkages have shown greater promise. U.S. Pat. No. 5,149,797 describes chimeric oligonucleotides having a phosphorothioate core region interposed between methylphosphonate regions.

Various methodologies have been used to synthesize oligonucleotides containing methylphosphonate internucleoside linkages. Miller et al., Biochemistry 25: 5092–5095 (1986), discloses an early methodology using a polymer support. Agrawal and Goodchild, Tetrahedron Lett. 28: 3539–3542 (1987), teaches a more generally applicable phosphoramidite approach using a controlled pore glass (CPG) support. All of the existing approaches, however, are inherently limited by the susceptibilty of the methylphosphonate linkage to hydrolysis by base, which precludes the use of the usual deprotection step, which employs prolonged treatment with 28% ammonium hydroxide. Some attempts to deal with this problem have included the use of N-isobutyryl-protected cytidine nucleoside phosphonamidite monomers in conjunction with $dA^{bz}$ and $dG^{iBu}$ monomers, followed by deprotection using initial exposure of the oligomer to 10% ammonium hydroxide in acetonitrile/ethanol at room temperature, then prolonged exposure to ethylenediamine. Also used has been pretreatment of the protected oligonucleotide with hydrazine hydrate in pyridine/acetic acid, followed by prolonged exposure to ethylene diamine/ethanol. Although these approaches have provided somewhat inconvenient answers to certain problems, they have created problems of their own for large scale synthesis of chimeric oligonucleotides, which have segments of different internucleosidic linkages. For example, the $dG^{iBu}$-methylphosphonamidite monomer is insoluble in acetonitrile, which is the solvent commonly used with most other phosphoramidite monomers. Consequently, prior to each coupling step at which this monomer is added, it is necessary to thoroughly wash the monomer delivery lines and the synthesis column with a solvent in which the $dG^{iBu}$ monomer is soluble, such as anhydrous peroxide-free THF or $CH_3CN/CH_2Cl_2$, to avoid precipitation of this monomer in the delivery lines or column. There is, therefore, a need for new synthesis processes which will provide convenient synthesis of chimeric oligonucleotides containing methylphosphonate internucleoside linkages in conjunction with other types of internucleoside linkages. Ideally, such a process should provide a convenient single step deprotection, should allow all of the monomers to be delivered in the same solvent, and should be adaptable to different chemical synthesis approaches.

BRIEF SUMMARY OF THE INVENTION

The invention provides new reagents and an improved process for synthesizing oligonucleotides containing alkylphosphonate internucleoside linkages. The process according to the invention provides convenient synthesis of chimeric oligonucleotides containing methylphosphonate internucleoside linkages in conjunction with other types of internucleoside linkages. The process according to the invention provides a convenient single step deprotection which, for solid phase synthesis also results in cleavage of the oligonucleotide from the solid support. In the process according to the invention, all of the monomers are soluble in, and can be delivered in the same solvent. Finally, the process according to the invention is readily adaptable to the various commonly used chemical synthesis approaches and to new approaches.

In a first aspect, the invention provides new nucleoside monomer synthons for introducing an alkylphosphonate internucleoside linkage into an oligonucleotide. The nucleoside monomer synthons according to the invention have the general structure:

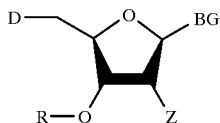

wherein B is a nucleoside base, D is a 5'-OH blocking group, R is an alkylphosphonamidite group, Z is hydrogen, —OG, —NG2, halogen, an —O-lower alkyl group containing 1–6 saturated or unsaturated carbon atoms, an —O-aryl or allyl group having 2–6 carbon atoms, wherein such alkyl, aryl or allyl group may be unsubstituted or may be substituted, e.g., with halogen, trifluoromethyl, cyano, nitroG, acylg, acyloxyG, alkoxyG, carboxyG, carbalkoxyG; and the protecting group (G) has the structure:

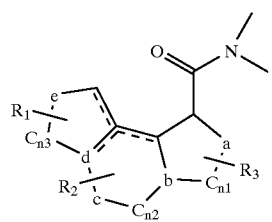

wherein $n_1$, $n_2$ and $n_3$ are each independently 0–10, wherein a, b, c, d and e are each independently hydrogen, carbon or nitrogen, and wherein the ring structure bearing substituent $R_3$ shown may be aromatic or heterocyclic, wherein the nitrogen displayed is the protected amino moiety of the nucleoside base, wherein $R_1$, $R_2$ and $R_3$ are independently hydrogen, or an alkyl, aryl, aralkyl, ether, hydroxy, nitrile, nitro, ester, carboxyl, or aldehyde group, and wherein dotted lines represent alternative exocyclic or endocyclic double bonds. In a preferred embodiment, a is hydrogen when $n_1$ is 0 and is carbon or nitrogen when $n_1$ is 1–10, b is hydrogen when $n_1$ and $n_2$ are both 0 and is carbon or nitrogen when either or both $n_1$ and $n_2$ are 1–10, c is hydrogen when $n_2$ is 0 and is carbon or nitrogen when $n_2$ is 1–10, and e is hydrogen when $n_3$ is 0 and is carbon or nitrogen when $n_3$ is 1–10. In a particularly preferred embodiment, $n_1$, $n_2$ and $n_3$ are each 0, and a, b, c, d and e are each hydrogen, and the protecting group takes the form N-pent-4-enoyl, i.e., $CH_2=CH(CH_2)_2CO$. These protecting groups protect the nucleoside base amino moieties by forming amide linkages, as in:

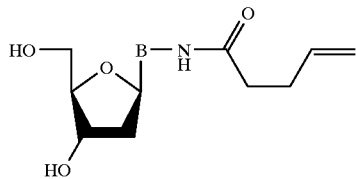

where the nitrogen displayed is the protected amino moiety of the base B.

In a second aspect, the invention provides a new and improved process for synthesizing oligonucleotides containing alkylphosphonate internucleoside linkages. This new process comprises sequentially coupling nucleoside synthons according to the invention to produce a base-protected oligonucleotide having an alkylphosphonate internucleoside linkage, followed by deprotection using a chemoselective removing agent. In other coupling steps, the process according to the invention can utilize any known or otherwise suitable oligonucleotide synthesis chemistry, including the well known H-phosphonate, phosphotriester and phosphoramidite chemistries.

The use of this new process provides numerous advantages. For example the process's mild procedure for removing the protecting group without affecting the integrity of other functionalities present in the oligonucleotide makes it possible to prepare novel analogs of oligonucleotides containing alkylphosphonate internucleoside linkages, and optionally containing other base sensitive functionalities, such as ribonucleosides, alkylphosphotriester linkages, certain base-sensitive phosphoramidate linkages, and other base-sensitive functionalities. Besides being able to synthesize oligonucleotides bearing additional "sensitive" functionalities, it can generally be used in the routine synthesis of various oligonucleotides containing alkylphosphonate internucleoside linkages.

In a third aspect, the invention provides useful intermediates for oligonucleotide synthesis. Such intermediates are oligonucleosides having nucleoside bases protected by a novel protective group according to the invention. Such oligonucleosides may have from two to about 25 nucleosides, and may be either support-bound or free in solution. The oligonucleosides according to this aspect of the invention may have alkylphosphonate or alkylphosphonite (III) internucleoside linkages. Optionally, the oligonucleosides may have other reactive functionalities protected by an appropriate protecting groups.

DETAILED DESCRIPTION OF THE PREFERRED EMBODIMENTS

Figure 1:
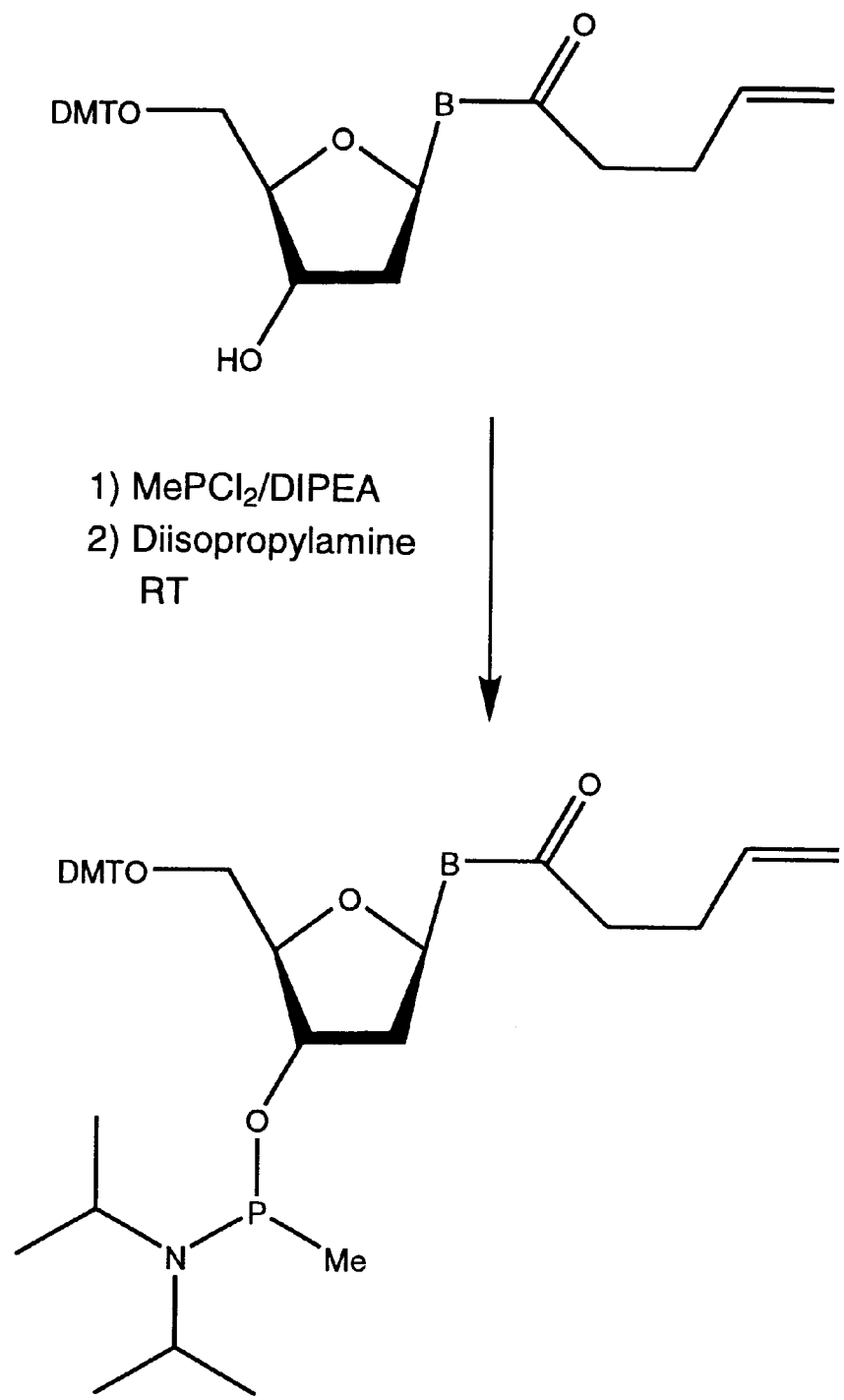
FIG. 1 shows a synthesis scheme for a preferred embodiment of a nucleoside monomer synthon according to the invention. In this illustration B is a nucleoside base and DMTO is dimethoxytrityl.

The invention relates to modified oligonucleotides that are useful for studies of gene expression and for the antisense therapeutic approach. In particular, the invention relates to the synthesis of such modified oligonucleotides containing alkylphosphonate internucleoside linkages. The patents and publications identified in this specification are within the knowledge of those skilled in this field and in their entirety.

The invention provides new reagents and an improved process for synthesizing oligonucleotides containing alkylphosphonate internucleoside linkages. The process according to the invention provides convenient synthesis of chimeric oligonucleotides containing methylphosphonate internucleoside linkages in conjunction with other types of internucleoside linkages. The process according to the invention provides a convenient single step deprotection which, for solid phase synthesis also results in cleavage of the oligonucleotide from the solid support. In the process according to the invention, all of the monomers are soluble in, and can be delivered in the same solvent. Finally, the process according to the invention is readily adaptable to the various commonly used chemical synthesis approaches and to new approaches.

In a first aspect, the invention provides new nucleoside monomer synthons for introducing an alkylphosphonate internucleoside linkage into an oligonucleotide. For purposes of the invention, the term "alkylphosphonate" means a phosphonate having a lower alkyl group containing 1–6 saturated or unsaturated carbon atoms, or an allyl group having 2–6 carbon atoms, wherein such alkyl or allyl group may be unsubstituted or may be substituted, e.g., with halogen, hydroxy, trifluoromethyl, cyano, nitro, acyl, acyloxy, alkoxy, carboxyl, carbalkoxyl, or amino groups. The nucleoside monomer synthons according to the invention have the general structure:

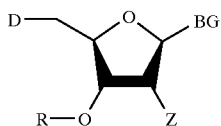

wherein B is a nucleoside base, D is a 5'-OH blocking group (see e.g. Sonveaux in *Methods in Molecular Biology, Vol 26: Protocols for Oligonucleotide Conjugates* pp. 28–36 (S. Agrawal, Ed., Humana Press, 1994), R is an alkylphosphonamidite group, Z is hydrogen, —OG, —NG2, halogen, a n —O-lower alkyl group containing 1–6 saturated or unsaturated carbon atoms, an —O-aryl or allyl group having 2–6 carbon atoms, wherein such alkyl, aryl or allyl group may be unsubstituted or may be substituted, e.g., with halogen, trifluoromethyl, cyano, nitroG, acylG, acyloxyG, alkoxyG, carboxyG, carbalkoxyG; and the protecting group (G) has the structure:

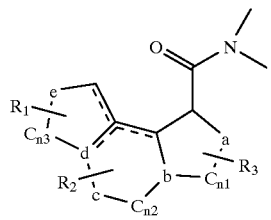

wherein $n_1$, $n_2$ and $n_3$ are each independently 0–10, wherein a, b, c, d and e are each independently hydrogen, carbon or nitrogen, and wherein the ring structure bearing substituent $R_3$ shown may be aromatic or heterocyclic, wherein the nitrogen displayed is the protected amino moiety of the nucleoside base, wherein $R_1$, $R_2$ and $R_3$ are independently hydrogen, or an alkyl, aryl, aralkyl, ether, hydroxy, nitrile, nitro, ester, carboxyl, or aldehyde group, and wherein dotted lines represent alternative exocyclic or endocyclic double bonds (i.e., any one of the dotted double bonds is present). In a preferred embodiment, a is hydrogen when $n_1$ is 0 and is carbon or nitrogen when $n_1$ is 1–10, b is hydrogen when $n_1$ and $n_2$ are both 0 and is carbon or nitrogen when either or both $n_1$ and $n_2$ are 1–10, c is hydrogen when $n_2$ is 0 and is carbon or nitrogen when $n_2$ is 1–10, and e is hydrogen when $n_3$ is 0 and is carbon or nitrogen when $n_3$ is 1–10. In a particularly preferred embodiment, $n_1$, $n_2$ and $n_3$ are each 0, and a, b, c, d and e are each hydrogen, and the protecting group takes the form N-pent-4-enoyl, i.e., $CH_2=CH(CH_2)_2CO$. These protecting groups protect the nucleoside base amino moieties by forming amide linkages, as in:

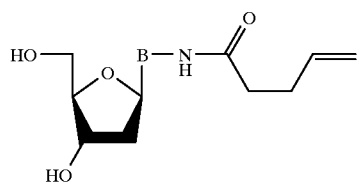

where the nitrogen displayed is the protected amino moiety of the base B.

In a second aspect, the invention provides a new and improved process for synthesizing oligonucleotides containing alkylphosphonate internucleoside linkages. This new process comprises sequentially coupling a nucleoside synthon according to the invention with a nucleoside or oligonucleoside having a free 5' hydroxyl group to produce a base-protected oligonucleotide having an alkylphosphonite (III) internucleoside linkage having as a bridging oxygen the oxygen from the free 5' hydroxyl group from the nucleoside or nucleotide, followed by oxidation of the internucleoside linkage to an alkylphosphonate linkage and deprotection using a chemoselective removing agent. As used herein, the terms "nucleoside" or "oligonucleoside" include those having appropriately protected reactive functionalities, either in accordance with the present invention or with conventional protecting groups known in the art (see e.g. Sonveaux in *Methods in Molecular Biology, Vol 26: Protocols for Oligonucleotide Conjugates* pp. 1–36 (S. Agrawal, Ed., Humana Press, 1994). Preferably, the oxidation of the internucleoside linkage to an alkylphosphonate linkage utilizes a phosphite oxidizing agent such as tert-butyl hydroperoxide or other well known agents (see Beaucage and Iyer, Tetrahedron 48: 2223–2311 (1992)). The term "chemoselective removing agent" means an agent that is capable of removing a base protecting group according to the invention without cleaving internucleosidic bonds, glycosidic bonds or other chemical bonds, except, optionally for solid phase synthesis, a chemical bond between the 3' terminal nucleoside of the oligonucleotide and the solid support. In certain preferred embodiments, the chemoselective removing agent is selected from the group consisting of halogens, especially $Br_2$, $Cl_2$ and $I_2$, any of which are preferably taken up in water, or in pyridine/ROH, wherein R is an alkyl, aralkyl or aryl group having 1–10 carbon atoms, or as an N-halosuccinimide. In alternative embodiments, non-chemoselective reagents may be used, such as aqueous ammonium hydroxide, alcoholic ammonia, alkali carbonates in organic solvents, primary or secondary amines, alkali hydroxides, or any amidolytic reagent, i.e., a chemical or enzymatic agent capable of hydrolyzing an amide linkage. For purposes of the invention, the term "chemoselective removing agent" encompasses such normally non-chemoselective reagents when they are used under conditions under which they behave as chemoselective removing agents, e.g., 28% aqueous ammonium hydroxide for 1 hour at room temperature. Those skilled in the art will recognize that determination of when such chemoselective removing agent behavior is present requires only routine experimentation.

In other coupling steps, the process according to the invention can utilize any known or otherwise suitable oligonucleotide synthesis chemistry, including the well known H-phosphonate, phosphotriester and phosphoramidite chemistries.

The use of this new process provides numerous advantages. For example the process's mild procedure for removing the protecting group without affecting the integrity of other functionalities present in the oligonucleotide makes it possible to prepare novel analogs of oligonucleotides containing alkylphosphonate internucleoside linkages, and optionally containing other base sensitive functionalities, such as ribonucleosides, alkylphosphotriester linkages, certain base-sensitive phosphoramidate linkages, and other base-sensitive functionalities. Besides being able to synthesize oligonucleotides bearing additional "sensitive" functionalities, it can generally be used in the routine synthesis of various oligonucleotides containing alkylphosphonate internucleoside linkages.

The process according to the invention can utilize and can be utilized in conjunction with any suitable oligonucleotide synthesis chemistry, including the well known H-phosphonate, phosphotriester and phosphoramidite chemistries. In one preferred embodiment, synthesis is carried out on a suitable solid support using either H-phosphonate chemistry, phosphotriester chemistry, phosphoramidite chemistry, or a combination of any of these (e.g., H-phosphonate chemistry for some cycles and phosphoramidite chemistry for other cycles). Suitable solid supports include any of the standard solid supports used for solid phase oligonucleotide synthesis, such as controlled-pore glass (CPG) and polymeric supports. (See, e.g., Pon, Methods in Molec. Biol. 20: 465 (1993)). Synthesis on such a solid support begins with coupling a nucleoside synthon according to the invention to a nucleoside that is covalently linked the solid support (i.e., linked to a functionality on the solid support, preferably an amino or hydroxyl functionality). More generally, the process according to the invention can be used with any of the chemistries commonly used for oligonucleotide synthesis, whether in solution phase or in solid phase.

This versatility of chemical synthetic approach of the process according to the invention makes the process according to the invention suitable for the synthesis of any of a broad class of compounds which contain at least one alkylphosphonate internucleoside linkage, all of which are referred to herein as "oligonucleotides". For purposes of the invention, the term oligonucleotide includes polymers of two or more deoxyribonucleotide, or 2'-O-substituted ribonucleotide monomers, or any combination thereof. Such oligonucleotides may optionally contain monomers which are coupled to each other by any of the numerous known internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halogen, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halogen group, but not with a 2'-H group.

In a third aspect, the invention provides useful intermediates for oligonucleotide synthesis. Such intermediates are oligonucleosides having one or more nucleoside base protected by a novel protecting group according to the invention, i.e., a protecting group having the structure:

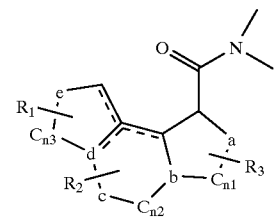

wherein $n_1$, $n_2$ and $n_3$ are each independently 0–10, wherein a, b, c, d and e are each independently hydrogen, carbon or nitrogen, and wherein the ring structure bearing substituent $R_3$ shown may be aromatic or heterocyclic, wherein the nitrogen displayed is the protected amino moiety of the nucleoside base, wherein $R_1$, $R_2$ and $R_3$ are independently hydrogen, or an alkyl, aryl, aralkyl, ether, hydroxy, nitrile, nitro, ester, carboxyl, or aldehyde group, and wherein dotted lines represent alternative exocyclic or endocyclic double bonds (i.e., any one of the dotted double bonds is present). In a preferred embodiment, a is hydrogen when $n_1$ is 0 and is carbon or nitrogen when $n_1$ is 1–10, b is hydrogen when $n_1$ and $n_2$ are both 0 and is carbon or nitrogen when either or both $n_1$ and $n_2$ are 1–10, c is hydrogen when $n_2$ is 0 and is carbon or nitrogen when $n_2$ is 1–10, and e is hydrogen when $n_3$ is 0 and is carbon or nitrogen when $n_3$ is 1–10. In a particularly preferred embodiment, $n_1$, $n_2$ and $n_3$ are each 0, and a, b, c, d and e are each hydrogen, and the protecting group takes the form N-pent-4-enoyl, i.e., $CH_2=CH(CH_2)_2CO$. Such oligonucleosides may have from two to about 25 nucleosides, and may be either support-bound or free in solution. The oligonucleosides according to this aspect of the invention may have alkylphosphonate or alkylphosphonite (III) internucleoside linkages. Optionally, the oligonucleosides may have a 3' leaving group, such as an H-phosphonate, phosphotriester, phosphoramidite or alkylphosphonamidite leaving group. Optionally, the oligonucleosides may have other reactive functionalities protected by an appropriate protecting groups (see e.g. Sonveaux in *Methods in Molecular Biology, Vol 26: Protocols for Oligonucleotide Conjugates* pp. 1–36 (S. Agrawal, Ed., Humana Press, 1994). In a preferred embodiment, such protecting group is a trityl or dimethoxytrityl group at the 5' end of the oligonucleoside.

Such oligonucleosides according to this aspect of the invention may conveniently be prepared by an adaptation the process according to the invention in which the step of treating the oligonucleoside with a chemoselective removing agent is omitted. The oligonucleosides according to this aspect of the invention are useful for synthesizing longer oligonucleosides by being coupled to other oligonucleosides by conventional techniques, such as the phosphoramidite, phosphotriester, or H-phosphonate approaches, or by any other coupling means.

The following examples are intended to further illustrate certain preferred embodiments of the invention and are not intended to limit the scope of the invention.

EXAMPLE 1

Preparation of N-pent-4-enoyl 2'-deoxy adenosine (dA Npr)

2'-Deoxyadenosine (Mallinkckrodt) (2.5 g, 10 mmol) was dried by repeated evaporation from anhydrous pyridine and was suspended in 50 ml of anhydrous pyridine. Trichloromethylsilane (64. ml, 50 mmol) was added and the reaction stirred for about 1 h. Then, 4-pentenoic anhydride (4 g, 20 mmol) was added and the contents stirred. After 15 min triethyl amine (3 ml) was added and the contents stirred for 2–3 h. The reaction slurry was cooled to 0–5° C. and 10 ml of water was added. After 5 min., 28% $NH_4OH$ (10 ml) was added. The resulting clear solution was evaporated to dryness. Water (150 ml) was added and the reaction mixture was extracted with ethylacetate: ether (50 ml, 1:1). The aqueous layer was separated and concentrated to a small volume. Upon leaving at room temperature, a white precipitate of the title compound was obtained. Filtration and drying gave ca. 3.5 g of pure title compound. Several experiments repeating the above procedure, using larger scale of operation, gave the title compound in 85–90% yield.

The same general procedure was employed for the preparation of dG and dC protected nucleosides.

EXAMPLE 2

Preparation of 5'-O-DMT-N-4-pent-4-enoyl-nucleosides

To 544 mg (1.63 mmol) of dA(N-pr) in 20 ml of anhydrous pyridine was added 1.108 g (3.3 mmol) of dimethoxytritylchloride. The reaction mixture was stirred at room temperature for 12 h. The reaction mixture was evaporated to dryness. The residue was chromatographed over silica gel 60 and eluted with $CH_2C12:CH_3OH:(Et)3N$ to give 0.73 g of 5'-O-DMT-N-4-pent-4-enoyl -2'-deoxyadenosine as a white foamy material.

EXAMPLE 3

Synthesis of Nucleoside Methylphosphonamidite Monomer Synthons

Nucleoside methylphosphonamidite monomer synthons were synthesized according to the scheme shown in FIG. 1. In this experiment, the nucleoside bases were cytidine, adenine and guanine. Methyldichlorophosphine (3 mmol) was dissolved in anhydrous methylene chloride (5 ml) under argon. Anhydrous diisopropylamine (6 mmol) was added to the solution via syringe at room temperature. The reaction mixture was rapidly stirred and a solution of the appropriate protected nucleoside monomers (1 mmol in 5 ml anhydrous methylene chloride containing 1.5 mmol N,N-diisopropylethylamine), prepared according to Examples 1 and 2 above, was added. The reaction was allowed to continue for 20 minutes, then 0.5 ml anhydrous methanol was added to destroy any residual chlorophosphonite. The reaction mixture was poured into 5% aqueous sodium bicarbonate and the product was extracted with methylene chloride (3×20 ml). The combined extracts were dried over anhydrous $Na_2SO_4$ and evaporated to dryness. The residue for each of the protected nucleoside methylphosphonamidite monomer synthons thus obtained was purified by silica gel column chromatography. Elution gave the desired product amidites as white foams after drying in vacuo. Yields were 84% for C, 92% for A and 54% for G. Analysis by $^{31}$P-NMR ($CDCl_3$, trimethylphosphate as external standard) and FAB-MS ($M^+$ ion) gave the expected results for each amidite. The $R_p/S_p$ ratio was about 60/40. Each of the nucleoside monomer synthons was readily soluble in anhydrous acetonitrile.

EXAMPLE 4

Synthesis of Methylphosphonate Dinucleosides

Thymidine nucleoside coupled to a CPG support by its 3' hydroxyl functionality was prepared according to standard procedures. In separate reactions, each of the nucleoside monomer synthons prepared according to Example 3 were coupled to the support-bound thymidine using conventional phosphoramidite chemistry. The coupling reaction yielded a support bound dinucleoside coupled by an internucleosidic methylphosphonite (III) linkage. This linkage was then oxidized using tert-butyl hydroperoxide (1 M in toluene) to yield a methylphosphonate internucleosidic linkage. The support-bound methylphosphonate dinucleosides were then treated with aqueous ammonium hydroxide (28%, 1 hour, room temperature) to remove the PNT protecting group and to cleave the dimers from the solid support. The dimers were obtained in yields of 94–96% as a mixture of $R_p$, $S_p$ diastereomers. Analysis by HPLC confirmed that the dimers were identical to dimer standards prepared from commercially available phosphonamidite monomers using both tert-butyl hydroperoxide and iodine as oxidants and employing manufacturer-recommended deprotection conditions. Further analysis by $^{31}$P-NMR and MALDI-TOF mass spectroscopy also proved the authenticity of the dimers produced according to this example (data not shown).

EXAMPLE 5

Synthesis of Chimeric Oligonucleotides Containing Methylphosphonate Internucleosidic Linkages Nucleoside monomer synthons prepared according to Example 3 were used under standard phosphoramidite coupling conditions to prepare chimeric oligonucleotides having methylphosphonate internucleosidic linkages in different numbers and at different positions. All syntheses were carried out on a 1–10 micromole scale. A first oligonucleotide had its 5 most 5' internucleosidic linkages as methylphosphonates, with the remaining 9 internucleosidic linkages as phosphodiesters. A second oligonucleotide had its 10 most 5' internucleosidic linkages as methylphosphonates, with the remaining 9 internucleosidic linkages as phosphodiesters. A third oligonucleotide had 10 phosphodiester internucleosidic linkages, followed by 4 methylphosphonate internucleosidic linkages, followed by 4 phosphodiester internucleosidic linkages. A fourth oligonucleotide had 5 phosphodiester internucleosidic linkages, followed by 4 methylphosphonate internucleosidic linkages, followed by 9 phosphodiester internucleosidic linkages. Following synthesis, the support-bound oligonucleotides were treated with aqueous ammonium hydroxide (28% for 1 hour at room temperature) to remove the phosphate and nucleoside base protecting groups and cleave the oligonucleotides from the support. Polyacrylamide gel electrophoresis revealed that these oligonucleotides had identical mobility to oligonucleotide standards of the same structure prepared using commercially available monomer synthons under the conditions recommended by the manufacturer. Surprisingly, HPLC analysis demonstrated that the monomer synthons according to the invention gave a superior product/failure sequence ratio, relative to the commercially available monomer synthons.

Those skilled in the art will recognize that many equivalents to the following claimed invention can be readily obtained by making insubstantial changes to the claimed invention. The following claims are intended to encompass all such equivalents.

What is claimed is:

1. A nucleoside monomer synthon having the structure:

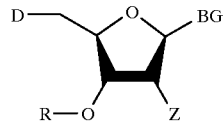

wherein B is a nucleoside base, D is a 5'-OH blocking group, R is an alkylphosphonamidite group, Z is hydrogen, —OG, —NG$_2$, halogen, an —O-lower alkyl group containing 1–6 saturated or unsaturated carbon atoms, or an —O-aryl or allyl group having 2–6 carbon atoms, wherein such alkyl, aryl or allyl group is unsubstituted or is substituted with halogen, trifluoromethyl, cyano, nitroG, acylG, acyloxyG, alkoxyG, carboxyG, carbalkoxyG, and wherein the nucleoside bases is protected by a protecting group G, wherein G is N-pent-4-enoyl.

2. An oligonucleoside alkylphosphonate or alkylphosphonite (III) having one or more nucleoside bases protected by a protecting group, wherein the protecting group is N-pent-4-enoyl.

* * * * *